US00PP30534P3

(12) United States Plant Patent
Hansen

(10) Patent No.: US PP30,534 P3
(45) Date of Patent: May 21, 2019

(54) ***SALVIA* PLANT NAMED 'AZURE SNOW'**

(50) Latin Name: ***Salvia pratensis* (Linnaeus)**
Varietal Denomination: Azure Snow

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/732,195

(22) Filed: Oct. 2, 2017

(65) Prior Publication Data

US 2019/0104672 P1 Apr. 4, 2019

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./263.1, 475
See application file for complete search history.

(56) References Cited

PUBLICATIONS

Walters Gardens, Inc. Summer 2017-Spring 2018 catalog. https://www.provenwinners.com/sites/provenwinners.com/files/images/professional/catalogs/1-intro-pw_perennials_2018.pdf. retrieved from the internet Oct. 15, 2018. 4 pages. (Year: 2017).*

* cited by examiner

*Primary Examiner* — Susan McCormick Ewoldt
*Assistant Examiner* — Karen M Redden

(57) ABSTRACT

The new and distinct cultivar of perennial *Salvia* plant named 'Azure Snow' characterized by its large flowers with violet-blue colored hood petals and white lower labium petals having a thin strong violet margin. Flowers are produced in late spring to early summer and repeat in late summer if deadheaded. The persistent dark green calyxes densely arranged in verticils fill in the full mounded habit with many stiff, upright, branched stems above large, rugose, dark-green foliage. 'Azure Snow' is useful for landscaping as a winter-hardy specimen plant, en masse or as a cut flower.

1 Drawing Sheet

Botanical denomination: *Salvia pratensis* (Linnaeus).
Cultivar designation: 'Azure Snow'.

BACKGROUND OF THE INVENTION

The present invention relates to a new and distinct cultivar of ornamental Sage plant hereinafter referred to by the cultivar name *Salvia* 'Azure Snow' or as the new plant. The new plant was from open pollinated seed collected by the inventor on Jun. 12, 2012 at a wholesale perennial nursery in Zeeland, Mich., USA. The female (seed) parent was a proprietary unreleased hybrid known as HK9-08-01 (not patented) and male (pollen) parent is 'Madeline' U.S. Plant Pat. No. 20,456. Seeds of the cross were harvested on Aug. 7, 2012 and given the breeder code 12-166-3 throughout the evaluation and comparison trials at the same nursery in Zeeland, Mich. The new plant passed the initial trials in 2014 and final trials in the summer of 2016 when it was approved for introduction. The plant was initially asexually propagated by basal vegetative shoot cuttings taken in 2014. The resulting plants of *Salvia* 'Azure Snow' asexually propagated at the same wholesale perennial nursery in Zeeland, Mich. have been found to be true to type and stable in successive generations.

No plants of *Salvia* 'Azure Snow' have been sold in this country, or anywhere in the world, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

Plants of *Salvia* 'Azure Snow' have not been observed under all possible environmental conditions. The phenotype may vary somewhat with variations in environment such as temperature, nutrition and light intensity, etc. without, however, any variance in genotype.

Compared with the female parent, the new plant has flowers that are violet-blue on the upper hood and white on the lower labium. Compared with the male parent, the new plant has similar flower color, but the peduncle verticils of the male parent are further separated, branches at wider angles and the habit is less compact. The nearest comparison cultivars are *Salvia* 'El Cielo Blue' (not patented) and *Salvia* patens 'Dot's Delight' (not patented). 'El Cielo Blue' and 'Dot's Delight' both have lower labium with white in the center and tube only.

The following characteristics in combination distinguish *Saliva* 'Azure Blue' as a new and distinct cultivar:

1. Large flowers with violet-blue colored upper hood petals and white lower labium petals with thin margin of strong violet;
2. Flowering from late spring into early summer and repeating in late summer when deadheaded;

3. Full mounded habit with many stiff, upright, branched flowering stems;
4. Calyces persistent, of dark green blushed with greyed purple in regions of high light;
5. Large, rugose, dark-green foliage;
6. Strong, vigorous and winter-hardy growth.

BRIEF DESCRIPTION OF THE DRAWINGS

The photographs of the new plant demonstrate the unique traits and the overall appearance of *Salvia* 'Azure Snow'. The colors are as accurate as reasonably possible with color reproductions. Variation in ambient light spectrum, source and direction may cause the appearance of minor variation in color. The plant used in the photographs was a two-year-old plant grown in an outdoor full-sun trial field at a wholesale perennial nursery in Zeeland, Mich. with supplemental water and fertilizer when needed. No plant growth regulators have been used.

DETAILED BOTANICAL DESCRIPTION

Figure 1:
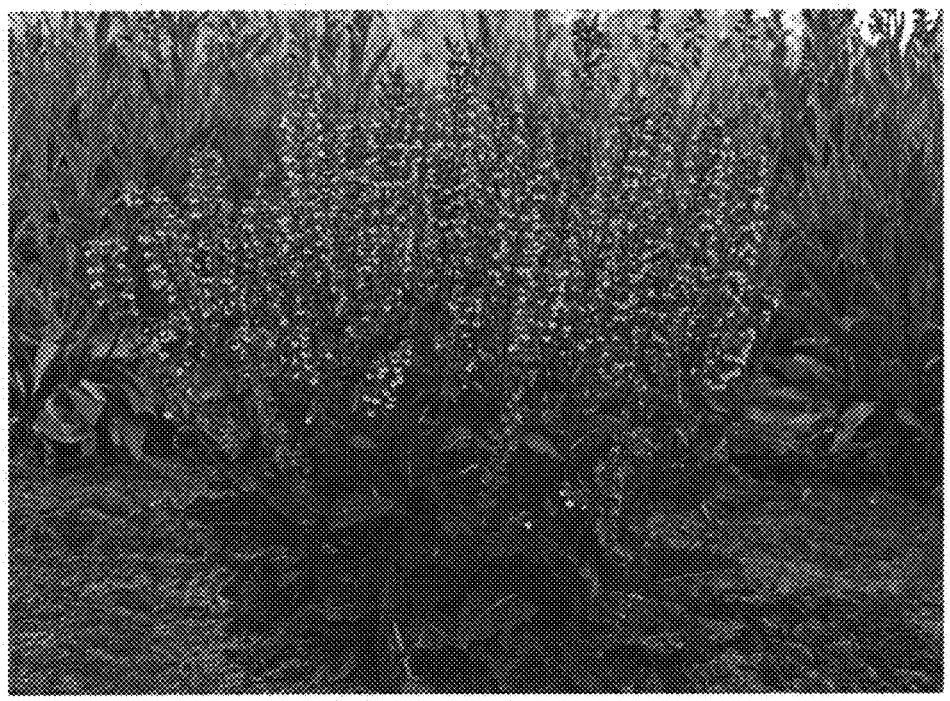
FIG. 1 shows the plant habit in full flower in a full-sun field.
Figure 2:
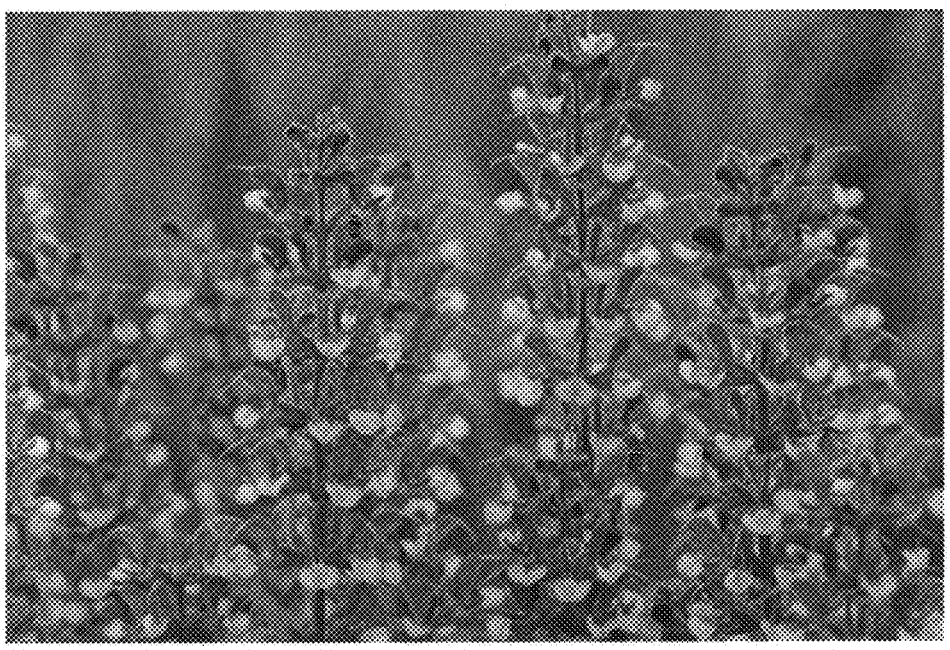
FIG. 2 shows a close-up of the flower scape with the buds, calyxes and upper hood petals of violet-blue color and lower labium of white with thin strong violet margin.

The following descriptions and color references except where common dictionary terms are used are based on the 2015 edition of The Royal Horticultural Society Colour Chart. *Salvia* 'Azure Snow' has not been observed under all possible environments. The phenotype may vary slightly with different growing environments such as temperature, light, fertility, soil pH, moisture and plant maturity levels, but without any change in the genotype. The following observations and size descriptions are based on two-year-old plants growing in a partially shaded greenhouse and also in a full-sun trial garden at a wholesale perennial nursery in Zeeland, Mich. Plants were given supplemental water and fertilizer but no plant growth regulators were used.

Botanical classification: *Salvia pratensis* (Linnaeus);

Parentage: Female or seed parent is the proprietary hybrid known as HK9-08-01; the male or pollen parent is 'Madeline';

Plant habit: Winter-hardy herbaceous perennial; multi-stemmed; with opposite foliage larger in basal portion and distally smaller; flowering in several tightly arranged verticils on branched upright racemes displayed above foliage; foliage extends up the stems to about two thirds the height of plant;

Propagation: By herbaceous, basal vegetative shoot cuttings; time to produce rooted shoots about two weeks;

Growth rate: Rapid, vigorous, finishing in a 65 mm container in about 7 weeks from rooted cutting; and flowering in a two-gallon container in about 8 weeks from a one-year-old plant;

Root description: Fine, well-branched; color dependent on age and soil type, from cream to dark tan in color; new roots in clean peat based soil nearest RHS 158A;

Foliage: Opposite; simple; rugose; lanceolate; surface glabrous adaxial and puberulent to pubescent abaxial; margin crenate; acute apex and base cordate to auriculate with lobes typically overlapping only in lower leaves; blades to about 14.0 cm long and about 5.5 cm across, decreasing in size distally; average about 10.0 cm long and 4.2 cm across; strong sage fragrance;

Foliage color: Young emerging leaves adaxial proximally between RHS 144A and RHS 144B and distally nearest RHS 137A, abaxial proximally between RHS 144A and RHS 144B and distally nearest RHS 137C; mature leaves adaxial nearest RHS 137A, abaxial surface between RHS 137B and RHS 137C;

Venation: Reticulate; impressed on adaxial side and costate on abaxial side; abaxial surface pubescent, main adaxial veins puberulent with secondary veins glabrous;

Vein color: Emerging adaxial nearest RHS 160D, abaxial nearest RHS 145C; mature adaxial midrib and primary veins between RHS 145C and RHS 145D, minor veins nearest RHS 137A, mature abaxial veins and midrib between RHS 137B and RHS 137C;

Petiole: Concavo-convex; adaxial and abaxial surfaces pubescent; to about 5.0 cm long and 6.0 mm wide, decreasing distally; pointing upwardly and outwardly;

Petiole color: Adaxial and abaxial surfaces between RHS 147C and RHS 147D;

Flower description: Perfect, bilabiate with fused base, verticillate with flowering generally beginning at lower verticils and advancing up the scape; with lower lip projected horizontal to slightly drooping and hood petal about 45 to 60 degree angle above horizontal; self-cleaning, petals not persistent; flowering beginning late spring for about three weeks and repeating after a four week rest if initial scapes removed; average about 22.0 mm long, 15.0 mm tall and 8.0 mm wide at lower lip;

Flower longevity: About four days on the plant or as cut flower;

Fragrance: No fragrance detected;

Flower buds one to two days prior to anthesis: Shape is oblong, laterally-flattened ellipsoid, rounded on top and slightly concave below, with rounded apex and base; pubescent; about 13.0 mm long, 5.0 mm tall and 3.0 mm wide;

Bud color: Exposed dorsal petal darker than RHS 90A and more purple than RHS N92D; ventral petal middle portion nearest RHS NN155D with blushing of nearest RHS N82D, distal portion of fused tube lighter than RHS N82D;

Petals: Bilabiate corolla with basal 8.0 mm fused into tube; upper petal folded laterally into hood; lower labium three lobed;

Hood (upper) petal: Abaxial petal surface puberulent distally and proximally glabrous, adaxial surface glabrous; upper hood petal fused to lower labium in basal 8.0 mm; upper hood petal and flattened side to side vertically, apex rounded; 15.0 mm long, 4.0 mm tall and 2.0 mm wide at fusion point;

Labium (lower petal): Lower labium of three lobes with two side lobes and one broad middle lobe; puberulent abaxial surface, glabrous adaxial; two side lobes slightly conduplicate with outer edges folded upward, acute apex and fused base, about 3.0 mm long and 2.5 mm wide when unfolded; center lobe concaved upwards, serrulate apex and fused base, puberulent abaxial and glabrous adaxial, about 5.0 mm wide in cupped form and 8.0 mm wide when flattened; labium about 15.0 mm long;

Petal color: Basal fused tube portion abaxial and adaxial nearest RHS NN155D and distal tube abaxial nearest RHS 90D, adaxial distal tube nearest RHS NN155D; upper hood petal abaxial nearest RHS 93B, upper hood adaxial nearest RHS 93B; lower labium petal outer side lobes nearest RHS 93B in both abaxial and adaxial, main lobe adaxial and abaxial nearest RHS NN155D with a thin margin less than 0.5 mm nearest RHS 93B along edges;

Androecium: Four, two longer and two shorter vestigial; bases adnate with labium, contained within hood petal;

*Filament*.—Glabrous; longer set arcuate downward along inside of upper hood, about 4.0 mm long free portion and 0.5 mm diameter; with vestigial set extending proximally about 180 degrees toward flower base, about 2.0 mm long and 0.5 mm diameter; color longer set nearest RHS 91A and vestigial set nearest RHS NN155D.

*Anther*.—On developed filaments only; glabrous, oblong, about 1.2 mm long and about 0.5 mm diameter; longitudinal, basifixed; color nearest RHS 165B.

*Pollen*.—Not observed.

Gynoecium: One, arcuate around inside of hood petal, about 22.0 mm long and protruding in distal 4.0 mm when mature;

*Style*.—About 19.0 mm long and about 0.5 mm diameter; color base nearest RHS NN155D, developing distally to nearest RHS 90C before stigma split.

*Stigma*.—Bifurcate, curved in the terminal 1.0 mm; apex pointed; color abaxial nearest RHS 90C, adaxial nearest RHS 90A.

*Ovary*.—Four, globose; superior; color nearest RHS 146B.

*Fruit*.—Nutlet, up to four at base inside calyx; rounded, about 1.2 mm diameter; color nearest RHS 200A.

Calyx: Five sepals, three upper and two lower, campanulate, apex acute; fused base; tube about 8.0 mm long and 5.0 mm tall at sepal tips and 4.0 mm wide; lower set separated in distal 2.5 mm; upper set of three fused sepals to about 1.0 mm of apex;

Calyx color: Abaxial upper three nearest RHS 146C and lower pair nearest RHS 146D with veins and blushed nearest RHS N186B; adaxial base nearest RHS 145D, distally nearest RHS 146D with veins nearest RHS 146B;

Bracts: Each verticil subtended by two opposite bracts; apex acuminate, base truncate, shape nearly cordate; margin minutely pubescent, and glabrous above and below; bract size up to 9.5 mm long and 8.0 mm wide, decreasing distally;

Bract color: Both surfaces nearest RHS 137A with midrib nearest RHS 145D;

Peduncles: Quadrangular, finely pubescent; about 10 per plant; strong; mostly upright, to about 50.0 cm tall and 5.0 mm across at base; flowering in upper 20.0 cm with about 90 flowers per central main stem; branches upright at lower nodes with branches to about 30.0 cm long and 3.0 mm across; average distance between verticils about 17.0 mm, greater proximally and less distally;

Peduncle color: Between RHS 144A in upper and lower regions;

Pedicels: Terete; puberulent; about 2.0 mm long and 0.5 mm diameter; held about 30 to 45 degrees above horizontal;

Pedicel color: Nearest RHS 145A;

Disease and pest resistance: Plants of *Salvia* 'Azure Snow' perform best with adequate moisture and good drainage; are hardy from USDA zone 3 to 8; resistant to diseases and pests beyond that common to *Salvia* has not been noted;

It is claimed:

1. The new and distinct perennial *Salvia* plant named 'Azure Snow' as herein described and illustrated.

* * * * *